United States Patent [19]
Conn

[11] 3,932,655
[45] Jan. 13, 1976

[54] SURGICAL SKIN SCRUB
[75] Inventor: Richard H. Conn, Detroit, Mich.
[73] Assignee: International Pharmakon Laboratories, Inc., Detroit, Mich.
[22] Filed: Apr. 8, 1974
[21] Appl. No.: 458,549

Related U.S. Application Data
[63] Continuation of Ser. No. 289,089, Sept. 14, 1972, abandoned.

[52] U.S. Cl. ............... 424/317; 424/319; 424/325; 424/329
[51] Int. Cl.² .......................................... A01N 9/00
[58] Field of Search ............ 424/317, 329, 319, 325

[56] References Cited
UNITED STATES PATENTS

| | | | |
|---|---|---|---|
| 3,052,604 | 9/1962 | Davis et al. | 424/329 |
| 3,472,939 | 10/1969 | Petrocci et al. | 424/329 |
| 3,525,793 | 8/1970 | Petrocci et al. | 424/329 |
| 3,694,262 | 9/1972 | Casey | 424/329 |
| 3,694,365 | 9/1972 | Castner | 424/329 |

FOREIGN PATENTS OR APPLICATIONS

| | | | |
|---|---|---|---|
| 937,937 | 9/1963 | United Kingdom | 424/329 |
| 1,578,111 | 7/1969 | France | 424/329 |

*Primary Examiner*—Frederick E. Waddell
*Attorney, Agent, or Firm*—Basile and Weintraub

[57] ABSTRACT

A disinfecting concentrate includes a mixture of n-alkylated benzalkonium halides, preferably, n-alkylated benzyl ammonium chlorides or benzalkonium chlorides, each having from 8 to 18 carbon atoms in their respective alkyl portions, preferably 12 to 18 carbon atoms, and mixtures thereof. The concentrate further includes a preservative and water. Use solutions prepared from the concentrate contain minor amounts thereof in order to be efficacious.

4 Claims, No Drawings

SURGICAL SKIN SCRUB

This is a continuation of copending application Ser. No. 289,089, filed Sept. 14, 1972, now abandoned.

BACKGROUND OF THE INVENTION

1. Field of the Invention

The present invention pertains to disinfecting compositions. More particularly, the present invention pertains to disinfecting concentrates and use solutions thereof. Even more particularly, the present invention relates to disinfecting concentrates and use solutions thereof based on n-alkylated benzyl ammonium halides or benzalkonium halides.

2. Prior Art

There has been developed over the years a plurality of disinfectant compositions prepared from concentrates thereof. Generally speaking, though, these compositions are restricted in their field of use, i.e. agricultural environments, industrial environments, household or domestic usage and the like.

The present invention, on the other hand, provides a disinfectant concentrate which can be utilized in plurality of environment based on use solutions thereof.

SUMMARY OF THE INVENTION

In accordance with the present invention, a detergent concentrate has for its active ingredient a composition which consists essentially of (1) a mixture of three n-alkylated benzyl ammonium halides, each of which has from 8 to 18 carbon atoms or mixtures thereof in its alkyl portion, and (2) a preservative which also functions as a chelating agent.

The active ingredient is then blended with emollients, surfactants, hydrotropes, and the like to prepare the final concentrate.

From the final concentrate a use solution is prepared with water, the concentrate being efficacious over a normal use range of from about 100 to 1500 ppm, based on one million parts of use solution.

The use solutions hereof can be effectively employed as household disinfectants; marine disinfectants, swimming pool sanitizers, surgical scrubs and skin cleansers for the treatment of dicubitous ulcers, and the like.

For a more complete understanding of the present invention, reference is made to the following detailed descriptions and examples thereof.

DESCRIPTION OF THE PREFERRED EMBODIMENTS

In accordance with the present invention a disinfectant concentrate consists essentially of:

1. from about 99 to 99.9 percent by weight of inert ingredients, such as, water, emollients, surface active agents (surfactants) hydrotropes and the like, and
2. from about 0.1 to 1 percent by weight of active ingredient, based on the total weight of the composition.

Preferably, the concentrate consists essentially of from about 99.5 to 99.9 percent by weight of inert ingredients and from about 0.1 to 0.5 percent of active ingredient.

The active ingredient contemplated for use herein consists essentially of a mixture of:

a. a chelating agent and
b. a mixture of n-alkylated benzyl alkyl ammonium halides or n-alkylated benzyl alkyl ammonium halides or n-alkyl benzalkonium halides.

The chelating agent deployed herein is, preferably, either ethylenediamine tetraacetic acid or the alkali metal salts thereof such as disodium ethylene diamine tetraacetic acid. Other useful compounds include the sugar acids or alkali metal salts thereof, such as, gluconic acid, lactic acid, citric acid, sodium or potassium gluconate, lactate, citrate and the like.

As noted, though, either ethylenediamine tetraacetic acid or the disodium salt thereof is the preferred chelating agent.

The n-alkyl benzalkonium halides contemplated for use herein correspond to the general formula:

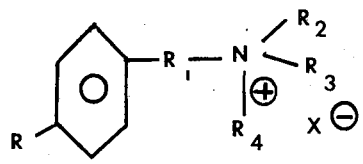

wherein R is hydrogen or lower alkyl having from 1 to 2 carbon atoms, $R_1$ is lower alkyl having from about 1 to 4 carbon atoms, $R_2$ and $R_3$ are each, individually, lower alkyl having from 1 to 2 carbon atoms, preferably, 1 carbon atom, $R_4$ is n-alkyl having from 8 to 18 carbon atoms or mixtures thereof, an X is halogen. Preferably, in the practice of the present invention R is hydrogen or lower alkyl having up to two carbon atoms, $R_1$ is alkyl having from 1 to 2 carbons, $R_2$ and $R_3$ are, each, alkyl having one carbon atom, $R_4$ is n-alkyl having from about 10 to 18 carbon atoms and mixtures thereof, and X is chlorine.

As is known to those skilled in the art, these compounds, which are quaternary ammonium halides, are generally prepared by the reaction of an alkyl halide with a tertiary amine, e.g. a benzyldialkylamine or a ethylbenzyldialkylamine. The tertiary amino compounds are, generally, prepared by the reaction of either ethylbenzyl chloride or benzylchloride with ammonia to form a secondary benzylamine or ethylbenzylamine. This secondary amine is then reacted with an alkyl chloride, e.g. methylchloride, to form the tertiary amine, and as contemplated herein, either dimethylbenzylamine or dimethylethylbenzylamine. All these reactions are on a molar basis.

In preparing the present benzalkonium compounds, the starting material is usually an N, N-dialkybenzylamine which is a commercially available product.

The preferred compounds, the quaternary ammonium chlorides are also, usually, commercially available products.

It has been found in the practice of the present invention that a mixture of three particular quaternary ammonium chlorides is extremely efficacious. The first two such compounds can be designated as:

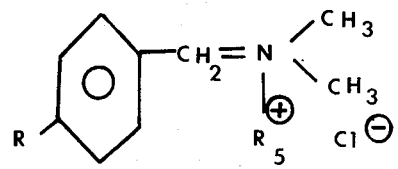

wherein R is hydrogen and $R_5$ is n-alkyl having from 12 to 18 carbon atoms and mixtures thereof. These compounds are prepared by the above defined procedure, using a commercially available mixture of n-alkyl chlorides, having a distribution of $C_{12}$— 0 to 10 percent; $C_{13}$ — 0 to 10 percent; $C_{14}$ — 0 to 90 percent; $C_{15}$ — 0 to 90 percent; $C_{16}$ — 0 to 50 percent; $C_{17}$ — 0 to 10 percent; $C_{18}$ — 0 to 10 percent, which are reacted with dialkylbenzylamine. The resulting quaternary compounds are commercially available compounds, and are sold under varying tradenames.

It is apparent that each one of the compounds, is in and of itself a mixture of quaternary ammonium chlorides, due to the distribution of n-alkyl groups in the alkyl chloride used to prepare it. Within the broad classification, two preferred products are found. The first preferred compound is prepared from an alkyl chloride having the following weight distribution: $C_{12}$ about 5 percent; $C_{14}$ about 60 percent; $C_{16}$ about 30 percent; and $C_{18}$ about 5 percent; the second preferred compound has an n-alkyl weight distribution of $C_{12}$ about 50 percent; $C_{14}$ about 30 percent; $C_{16}$ about 15 percent; and $C_{18}$ about 5 percent.

The third quaternary ammonium chloride used in the present composition corresponds to the formula:

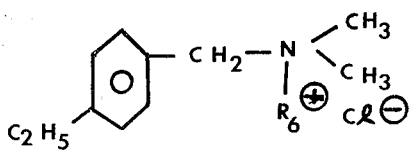

wherein $R_6$ is n-alkyl having from about 12 to 14 carbon atoms and mixtures thereof. As above, these compounds are prepared by reacting the dialkylethylbenzylamine with a molar quantity of n-alkyl chloride, wherein the alkyl portion thereof comprises a mixture of n-alkyl groups having a general weight distribution of $C_{12}$ — 0 to 90 percent; $C_{13}$ — 0 to 50 percent; $C_{14}$ — 0 to 50 percent; and, preferably, having weight distribution of $C_{12}$ — 65 to 75 percent, and $C_{14}$ — 25 to 35 percent. Also, as above, this benzalkonium chloride is a commercially available product.

In formulating the present active ingredient a weight ratio of quaternary ammonium chlorides of about 2:1:2 is employed. The active ingredient contains from about 50 to 75 percent, by weight, of the mixture of quaternary ammonium chlorides and from about 25 to 50 percent by weight of chelating agent. Preferably, the active ingredient contains from about 50 to 60 percent by weight of the mixture of quaternary ammonium chlorides and from about 40 to 50 percent by weight of chelating agent.

In preparing the disinfectant concentrate, as noted, above, the active ingredient is mixed, under ambient conditions, with the inert ingredients such as surfactants, emollients, corrosion inhibitors and the like.

The useful surfactants can be either nonionic, cationic, anionic, amphoteric, as well as mixtures thereof. Preferred surfactants are the amphoteric and anionic surfactants as well as mixtures thereof. Suitable amphoteric surfactants are those which co-act as emulsifiers, such as, the alkylated amino propionic acid derivatives, such as, the neutralized alkali metal salts thereof. Exemplifying such compounds are the sodium salt of N-coco-B-amino propionate, N-lauryl-, N-myristyl- and the like, as well as the dialkali metal salts of the alkylated amino propionic acid derivates, such as, disodium - N-tallow-B-amino dipropionate.

Useful anionic surfactants are those which, also, function as corrosion inhibitors. Suitable anionic surfactants are the alkanolamines, such as, ethanolamine, diethanolamine, triethanolamine and the like.

The surfactants are generally deployed in a respective weight ratio of amphoteric to anionic surfactant of from about 50:1 to 100:1, with the total surfactant concentration in the concentrate or composition ranging from about 4 to 6 percent by weight, based on the total weight of the composition.

An emollient, such as, glycerine is, also, preferably, included within the final concentrate to prevent skin irritation to the user. The emollient is normally deployed in an amount ranging from about 3 to 5 percent based on the total weight of the composition.

The balance of the composition is water.

To prepare a use solution from the above-defined composition, the concentrate is mixed with water, under ambient conditions, to a minimum dilution of concentrate of at least 100 ppm of concentrate per one million parts of use solution. Generally, the concentrate will be present in the use solution in an amount ranging from about 100 to 2000 ppm thereof, and preferably 250 to 1500 ppm of concentrate per one million parts of use solution.

The present use solution has been found to be effective in killing off both gram-negative and Gram-positive bacterium and fungi such as, pseudomonas aeruginosa, trichophyton interdigitale strain 640, staphylococcus aureus, salmonella choleraesius, escherichia coli and other similar microbial contaminants. Thus, the present use solutions are effective disinfectants in hospitals, clinics, nursing homes, for cleaning dietary utensils, in industrial food processing plants and institutions, as an algae growth in swimming pools, as a surgical scrub and skin cleanser, and the like.

For a more complete understanding of the present invention reference is made to the following examples which are to be construed as exemplifying rather than limitative of the present invention. In the examples all parts are by weight absent indication to the contrary.

EXAMPLE I

Into a suitable vessel equipped with stirring means was added the following:

| INGREDIENT | AMOUNT, pbw |
| --- | --- |
| QUATERNARY AMMONIUM CHLORIDE A[1] | 0.050 |
| QUATERNARY AMMONIUM CHLORIDE B[2] | 0.025 |
| QUATERNARY AMMONIUM CHLORIDE C[3] | 0.050 |
| CHELATING AGENT[4] | 0.090 |
| | 0.215 |

These ingredients were then mixed to form a homogeneous mixture of active ingredients.

This active ingredient was then blended with the following inert ingredients.

| INGREDIENT | AMOUNT, pbw |
|---|---|
| AMPHOTERIC SURFACTANT[5] | 4.780 |
| GLYCERINE, as an emollient | 4.070 |
| ANIONIC SURFACTANT[6] | 0.148 |
| CHELATING AGENT[7] | 0.108 |
| WATER | 90.779 |
| | 99.785 |

The resulting product was a disinfecting composition in accordance with the present invention.

1. an n-Alkyl ($C_{12}$ 5%, $C_{14}$ 60%, $C_{16}$ 30%, $C_{18}$ 5%) dimethyl benzyl ammonium chloride;
2. an n-Alkyl ($C_{12}$ 50%, $C_{14}$ 30%, $C_{16}$ 17%, $C_{18}$ 3%) dimethyl benzyl ammonium chloride;
3. an n-Alkyl ($C_{12}$ 68%, $C_{14}$ 32%) dimethyl ethylbenzyl ammonium chloride;
4. the disodium salt of ethylene diamine tetraacetic acid;
5. sodium salt of N-coco-B-aminopropionate
6. triethanolamine
7. same as (4)

EXAMPLE II

The product of Example I was mixed with water containing 500 parts per million AOAC synthetic hard water to prepare a use solution thereof. The use solution, which contained 200 ppm of the mixture of alkylated benzalkonium chlorides, was then tested for effectiveness against staphylococcus aureus ATCC No. 6538.

The test method employed was a modification of the *Official Methods of Analysis of the AOAC*, Eleventh Edition, Chapter 4, paragraphs 4.023–4.032, using platings of $10^{-3}$, $10^{-4}$ and $10^{-5}$ dilution of the culture and a five-minute exposure period.

In addition to the product of Example I, similar tests were conducted using a sample of the product of Example I which was approximately one year old, and a sample which was heated to about 90°F.

After five minutes each sample demonstrated greater than 99.999 percent kill off of the inoculum, thus, evidencing the efficacy of the instant product.

I claim:
1. A surgical skin scrub of the type adapted for topical application to a user's skin consisting essentially of:
   a. from about 99.0 to 99.9 percent by weight of inert ingredients, and
   b. from about 0.1 to 1.0 percent by weight of an active ingredient consisting essentially of:
      1. from about 25 to 50 percent by weight of a chelating agent selected from the group consisting of ethylene diamine tetraacetic acid, disodium ethylene diamine tetraacetic acid, gluconic acid, lactic acid, citric acid, sodium gluconate, sodium lactate, sodium citrate, potassium gluconate, potassium lactate and potassium citrate, and
      2. from about 50 to 75% by weight of a mixture of three n-alkyl benzalkonium chlorides, the first and second of which are of the formula:

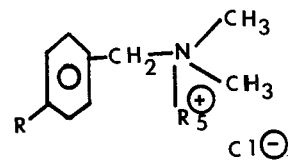

wherein R is hydrogen, $R_5$ is n-alkyl having from 12 to 18 carbon atoms or mixtures thereof, the first benzalkonium chloride having an $R_5$ distribution of $C_{12}$ about 5 percent; $C_{14}$ about 60 percent; $C_{16}$ about 30 percent and $C_{18}$ about 5 percent; the second benzalkonium chloride having an $R_5$ distribution of $C_{12}$ about 50 percent; $C_{14}$ about 30 percent; $C_{16}$ about 15 percent and $C_{18}$ about 5 percent; and the third benzalkonium chloride is of the formula:

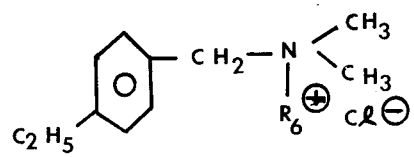

wherein $R_6$ is n-alkyl having a distribution of $C_{12}$ from 65 to 75 percent and $C_{14}$ from 25 to 35 percent, and wherein the benzalkonium chlorides are present in a respective weight ratio of about 2:1:2.

2. The skin scrub concentrate of claim 1 wherein the inert ingredients includes from about 4 to 6%, by weight, of a surfactant mixture consisting essentially of an amphoteric and anionic surfactant present in a respective weight ratio of from about 50:1 to 100:1.

3. The skin scrub concentrate of claim 2 wherein the amphoteric surfactant is an alkali metal salt of an alkylated amino propionate and the anionic surfactant is an alkanolamine.

4. A surgical skin scrub consisting essentially of:
an aqueous solution of the concentrate of claim 1, the aqueous solution containing from about 100 to 2000 parts per million, by weight, of the concentrate per million parts by weight of the scrub.

* * * * *